US008344161B2

(12) United States Patent
Hoffmann-Emery et al.

(10) Patent No.: US 8,344,161 B2
(45) Date of Patent: Jan. 1, 2013

(54) PROCESS FOR THE PREPARATION OF PYROLLIDINE-3-CARBOXYLIC ACIDS

(75) Inventors: Fabienne Hoffmann-Emery, Weil am Rhein (DE); Kurt Puentener, Basel (CH); Hasane Ratni, Habsheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 291 days.

(21) Appl. No.: 12/633,814

(22) Filed: Dec. 9, 2009

(65) Prior Publication Data
US 2010/0152462 A1     Jun. 17, 2010

(30) Foreign Application Priority Data
Dec. 16, 2008  (EP) .................................... 08171798

(51) Int. Cl.
C07D 207/04         (2006.01)
(52) U.S. Cl. ....................................... 548/531; 548/530
(58) Field of Classification Search .................. 548/530, 548/531
See application file for complete search history.

(56) References Cited

U.S. PATENT DOCUMENTS

| 3,004,058 | A | 10/1961 | Cunningham |
| 4,556,740 | A | 12/1985 | Hansen et al. |
| 5,302,738 | A | 4/1994 | Foricher et al. |
| 5,488,172 | A | 1/1996 | Cereghetti et al. |
| 5,663,191 | A | 9/1997 | Lavielle et al. |
| 6,046,207 | A | 4/2000 | Meyer et al. |
| 6,545,165 | B1 | 4/2003 | Fleming et al. |
| 6,552,204 | B1 | 4/2003 | Harrington et al. |
| 6,794,525 | B2 | 9/2004 | Bulliard et al. |
| 2006/0020011 | A1 | 1/2006 | Wu et al. |

FOREIGN PATENT DOCUMENTS

| EP | 0104375 | 4/1984 |
| EP | 0398132 | 11/1990 |
| EP | 0580331 | 1/1994 |
| EP | 1705176 | 9/2006 |
| WO | 9216535 | 10/1992 |
| WO | 9601831 | 1/1996 |
| WO | 0129031 | 4/2001 |
| WO | 0212253 | 2/2002 |
| WO | 02068388 | 9/2002 |
| WO | 2005068427 | 7/2005 |
| WO | 2007113155 | 10/2007 |

OTHER PUBLICATIONS

Yamamoto, et al., Comprehensive Asymmetric Catalysis, vol. I, p. 163 ff., Springer (1999).
Patane et al., Bioorg. Med. Chem. Lett. vol. 8, pp. 2495-2500 (1998).
Haight et al., Organic Process Research & Development vol. 8, 897-902 (2004).
Ujjainwalla et al., Bioorg. Med. Chem. Lett. vol. 13, 4431-4435, (Merck Sharp & Dohme) (2003).
Chung et al., J. Org. Chem.vol. 70, pp. 3592-3601 (Merck Sharp & Dohme) (2005).
Shen et al., Bioorg. Med. Chem. Lett. vol. 14, pp. 941-945 (Merck Sharp & Dohme) (2004).
Hale et al., Bioorg. Med. Chem. Lett. vol. 11, pp. 1437-1440 (Merck Sharp & Dohme) (2001).
Fevig et al., Bioorg. Med. Chem. Lett. vol. 9, pp. 1195-1200 (DuPont) (1999).
Kozikowski et al., The Journal of Pharmacology and Experimental Therapeutics vol. 305, pp. 143-150 (2003).
Heiser. et al., Tetrahedron: Asymmetry vol. 2, pp. 51-62 (1991).
Feiken et al., Organometallics vol. 16, pp. 537-543 (1997).
Genet J.-P., Acc. Chem. Res. vol. 36, pp. 908-918 (2003).
Experimental Chemistry, 4th edition, vol. 18, Organometallic complexes, pp. 339-344, Ed. Chemical Society of Japan, Maruzen (1991) (English language translation attached).
Benincori et al., J. Org. Chem. vol. 61, pp. 6244-6251 (1996).
Meyers et al., Org. Chem. vol. 58, pp. 36-42 (1993).
Tseng et al., Chem. Pharm, Bull. vol. 25, pp. 166-170 (1977).
Eckert et al., Synthetic Communications vol. 28, pp. 327-335 (1998).
Meyer et al., J. Med. Chem. vol. 44, pp. 1971-1985 (2001).
Hancock et al., The Journal of Pharmacology and Experimental Therapeutics vol. 300, No. 2, pp. 478-486 (2002).
Padwa et al., Tetrahedron vol. 41, No. 17, pp. 3529-3535 (1985).
Negron et al., Heterocycles vol. 34, No. 2, pp. 293-301 (1992).
Cottrell et al., J. Chem. Soc. Perkin Trans. pp. 1091-1097 (1991).
Horie et al., J. Org. Chem. vol. 57, pp. 3343-3347 (1992).
Caille J. C., Organic Process Research & Development vol. 6, pp. 471-476 (2002).
Dinsmore et al., Tetrahedron Letters vol. 40, pp. 3989-3990 (1999).
Taylor et al. J. Org. Chem. vol. 47, pp. 528-531 (1982).

(Continued)

Primary Examiner — Golam M M Shameem
(74) Attorney, Agent, or Firm — George W. Johnston; Patricia S. Rocha-Tramaloni; Kimberly J. Prior

(57) ABSTRACT

The invention relates to a novel process for the preparation of (3S,4S)- or (3R,4R)-1-benzyl-4-(halogen-aryl)-pyrrolidine-3-carboxylic acids of formula I

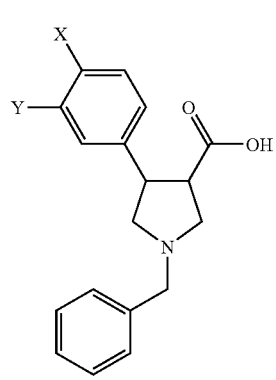

I or salts thereof, wherein X and Y are each independently hydrogen or a halogen atom, with the proviso that at least one of X or Y is a halogen atom. The compounds of formula I are useful as starting materials or intermediates for the preparation of pharmaceutically active compounds, especially for compounds, which are useful for the treatment of central nervous system disorders.

11 Claims, No Drawings

OTHER PUBLICATIONS

Taylor et al., J. Og. Chem. vol. 38, No. 16 pp. 2817-2821 (1973).
Taylor et al., J. Am. Chem. Soc. vol. 111, pp. 285-291 (1989).
Doyle et al., J. Org. Chem. vol. 42, No. 14, pp. 2426-2431 (1977).
Doyle et al., J. Org. Chem. vol. 45, pp. 2570-2575 (1980).
Bock et al. Annual Reports in Medicinal Chemistry, Chapter 20, pp. 221-230 (2000).
Garraway et al , The Lancet "High Prevalence of Benign Prostatic Hypertrophy in the Community" vol. 338 pp. 469-471 (1991).
Caine et al., British Journal of Urology, vol. 48 pp. 255-263 (1976).
Lepor et al., The Prostate, vol. 18 pp. 345-355 (1991).
Hedlund et al., The Journal of Urology "Effects of Prazosin in Patients with Benign Prostatic Obstruction" vol. 130 pp. 275-278 (1983).
Bendix Holme et al., Scand. J. Urol. Nephrol. vol. 28, pp. 77-82 (1994).
Hieble et al., Exp. Opin. Invest. Drugs, vol. 6(4) pp. 367-387 (1997).
Yamada et al., Clinical & Experimental Pharmacology & Physiology vol. 21, pp. 405-411 (1994).
Geissman, T. A. Organic Reactions vol. II, Chapter 3 (1944).
Johnson, J. R. Organic Reactions vol. I, Chapter 8 (1942) pp. 210-265.
Favini et al., Gazzetta Chimica Italiana vol. 89, pp. 2222-2231 (1959).
Freifelder et al., Journal of Pharmaceutical Sciences vol. 54 p. 1204 (1965).
Svela, G, Vogel's Qualitative Inorganic Analysis, 7th Ed. p. 132 (1996).
Brown et al., Tetrahedron Asymmetry 2(5), pp. 331-334 (1991).
Ratovelomanana-Vidal et al., Advanced Synthesis & Catalysis 345(1-2), pp. 261-274 (2003).
Ujjainwalla et al., Bioorganic & Medicinal Chem. Letters 13, pp. 4431-4435 (2003).
Repic, O., Principles of Process Research and Chemical Development in the Pharmaceutical Industry, pp. 72, and 89-93 (1998).
Benincori et al., J. Org. Chem. vol. 65, p. 2063 (2000).

PROCESS FOR THE PREPARATION OF PYROLLIDINE-3-CARBOXYLIC ACIDS

PRIORITY TO RELATED APPLICATION(S)

This application claims the benefit of European Patent Application No. 08171798.5, filed Dec. 16, 2008, which is hereby incorporated by reference in its entirety.

BACKGROUND OF THE INVENTION

A process for the preparation of enantiomerically enriched cyclic β-heteroaryl carboxylic acids via enantioselective hydrogenation has been described in the PCT Publication WO 2007/113155. The process was found to be unsatisfactory with regard to the reaction conditions needed, the achievable yield and the enantiomeric purity of the reaction product.

SUMMARY OF THE INVENTION

The invention provides a novel process for the preparation of (3S,4S)- or (3R,4R)-1-benzyl-4-(halogen-aryl)-pyrrolidine-3-carboxylic acids of formula I

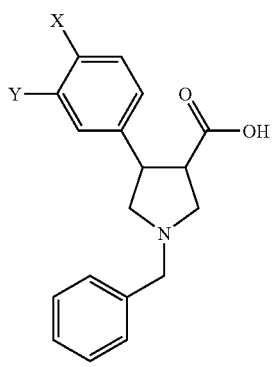

I or salts thereof,
wherein
X and Y are each independently hydrogen or a halogen atom, with the proviso that at least one of X or Y is a halogen atom.

The compounds of formula I are useful as starting materials or intermediates for the preparation of pharmaceutically active compounds, especially for compounds, that are useful for the treatment of central nervous system disorders (Bioorg. Med. Chem. Lett. 1999, 9, 195; Bioorg. Med. Chem. Lett. 2004, 14, 941).

The present invention therefore provides a more economical enantioselective hydrogenation method for the preparation of compounds of formula I, i.e. a method which can be carried out under moderate conditions and which results in high yields and high enantiomeric purity of the product.

More particularly, the present invention provides a process for the preparation of (3S,4S)-1-benzyl-4-halogen-aryl-pyrrolidine-3-carboxylic acids of formula I

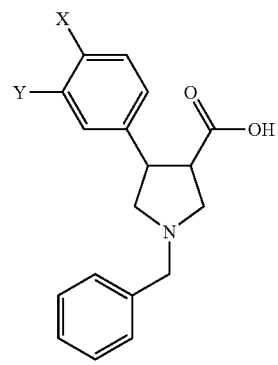

I or salts thereof,
wherein
X and Y are each independently hydrogen or a halogen atom, with the proviso that at least one of X or Y is a halogen atom, comprising a catalytic homogeneous enantioselective hydrogenation of a compound of formula II

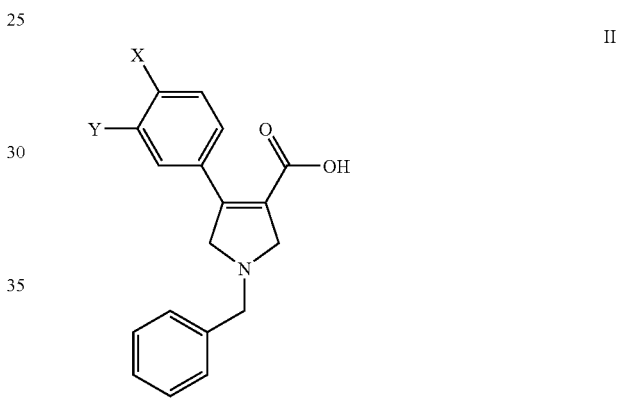

II or salts thereof,
wherein X and Y are as defined above, in the presence of a Ru-catalyst of the formula $$Ru(T)_2D \qquad III$$

wherein,
T represents the group $A\text{-}COO^-$,
A represents $C_{1-7}$-alkyl which is optionally substituted with halogen and
D represents a chiral diphosphine ligand.

DETAILED DESCRIPTION OF THE INVENTION

Unless otherwise indicated, the following definitions are set forth to illustrate and define the meaning and scope of the various terms used to describe the invention herein.

"Halogen" refers to fluorine, chlorine, bromine, or iodine. The term halogen used for X or Y preferably stands for chlorine or fluorine. In a further preferred embodiment X is chlorine or fluorine and Y is hydrogen, chlorine or fluorine. In an even more preferred embodiment X is chlorine and Y is hydrogen. The term "halogen" used for $R^3$ and/or $R^4$ refers to fluorine, chlorine, bromine and iodine, with fluorine, bromine and chlorine being preferred.

Accordingly preferred starting compounds of formula II are selected from:

1-benzyl-4-(4-chloro-phenyl)-2,5-dihydro-1H-pyrrole-3-carboxylic acid monohydrate;

1-benzyl-4-(3,4-dichloro-phenyl)-2,5-dihydro-1H-pyrrole-3-carboxylic acid;

1-benzyl-4-(3,4-difluoro-phenyl)-2,5-dihydro-1H-pyrrole-3-carboxylic acid; and 1-benzyl-4-(4-chloro-3-fluoro-phenyl)-2,5-dihydro-1H-pyrrole-3-carboxylic acid.

The term "$C_{1-7}$-alkyl", alone or in combination with other groups, refers to a branched or straight-chain monovalent hydrocarbon radical of one to seven carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Methyl and ethyl, particularly methyl, are especially preferred.

The term "$C_{1-7}$-alkyl optionally substituted with halogen" refers to a $C_{1-7}$-alkyl group as defined above wherein at least one of the hydrogen atoms of the alkyl group is replaced by a halogen atom, preferably fluoro or chloro. Among the preferred halogenated lower alkyl groups are trifluoromethyl, difluoromethyl, fluoromethyl and chloromethyl.

The term "$C_{1-7}$-alkoxy" refers to a group $C_{1-7}$-alkyl-O—, with the meaning of $C_{1-7}$-alkyl as above. Examples of $C_{1-7}$-alkoxy groups are e.g. methoxy, ethoxy, propoxy, isopropoxy, butoxy, isobutoxy and hexyloxy, with methoxy being especially preferred.

The term "di-$C_{1-7}$-alkylamino" refers to a group $(C_{1-7}\text{-alkyl})_2$-N—, where $C_{1-7}$-alkyl is as defined above. Examples of di-$C_{1-7}$-alkylamino groups are e.g. dimethylamino or diethylamino with dimethylamino being preferred.

The term "tri-$C_{1-7}$-alkylsilyl" refers to a group $(C_{1-7}\text{-alkyl})_3$-Si, where $C_{1-7}$-alkyl is as defined above. Examples of tri-$C_{1-7}$-alkylsilyl are e.g. trimethylsilyl or triethylsilyl, with trimethylsilyl being preferred.

The term "chiral diphosphine ligand" refers to a diphosphine in which the two tertiary phosphorus atoms are bound to different carbon atoms of linear or cyclic bridging groups, preferably bound to different carbon atoms of a carbon chain having from 2 to 8 carbon atoms, where the carbon chain may be part of a monocyclic ring or part of a bicyclic ring system (e.g. biphenyl, binaphthyl, bisthienyl or cyclopentadienylphenyl, cyclopentadienyl-$CH_2$-phenyl, cyclopentadienyl-$CH(OCH_3)$-phenyl in ferrocenes). Particularly, the chiral diphosphine ligand is a chiral ligand characterized by formula IVa, IVb, IVc, IVd, or IVe.

The starting compounds of formula II are accessible by the method provided in the scheme below:

Scheme 1:

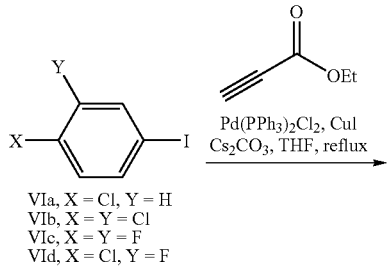

VIa, X = Cl, Y = H
VIb, X = Y = Cl
VIc, X = Y = F
VId, X = Cl, Y = F

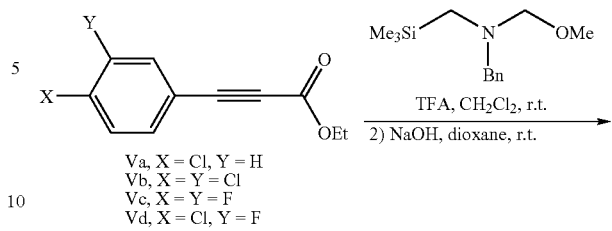

Va, X = Cl, Y = H
Vb, X = Y = Cl
Vc, X = Y = F
Vd, X = Cl, Y = F

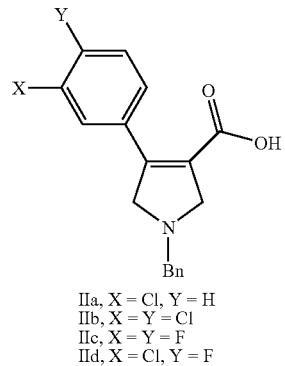

IIa, X = Cl, Y = H
IIb, X = Y = Cl
IIc, X = Y = F
IId, X = Cl, Y = F or can be prepared in analogy as described in J. Med Chem 1992, 233-241; THL 2004, 3265 or Org. Biomol. Chem. 2004, 2763.

The starting compound of formula II, i.e. the hydrogenation substrate, preferably is in the form of the free acid or the monohydrate thereof.

Alternatively the carboxylate, which can be formed from the free acid or even from a salt of the compound of formula II by conversion with a suitable base, can be used. Suitable bases usually are tertiary amines like tri-alkyl amines. Preferred base is triethylamine.

As outlined above the Ru-catalyst used for the catalytic homogeneous enantioselective hydrogenation has the formula $$Ru(T)_2D \qquad \text{III}$$

wherein,

T represents the group A-COO$^-$ wherein

A represents $C_{1-7}$-alkyl which is optionally substituted with halogen and

D represents a chiral diphosphine ligand.

T preferably is selected from $CH_3COO^-$ or $CF_3COO^-$ and more preferably stands for $CH_3COO^-$.

A preferably stands for methyl.

The chiral diphosphine ligand D is selected from the group consisting of

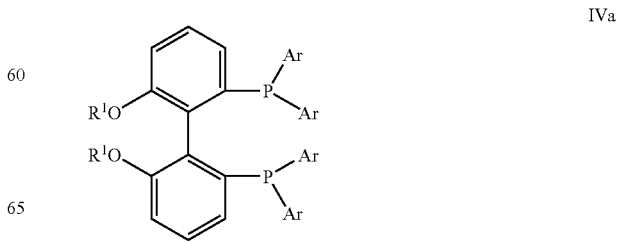

IVa

-continued

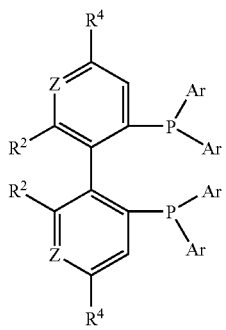

IVb

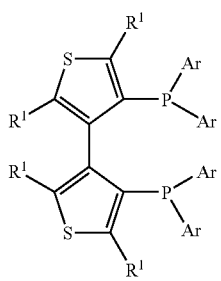

IVc

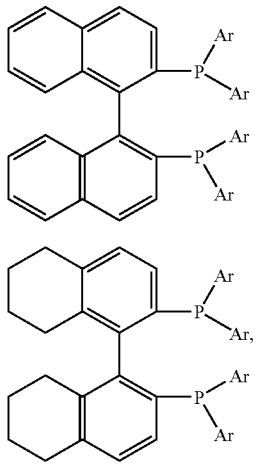

IVd

IVe wherein

Ar is 2-thienyl, 3-thienyl, 2-furyl, 3-furyl, phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl;

Z is N or C—$R^3$;

$R^1$ is $C_{1-7}$-alkyl;

$R^2$ is $C_{1-7}$-alkyl, $C_{1-7}$-alkoxy, hydroxy or —OC(O)—$C_{1-7}$-alkyl or —OC(O)-cyclohexyl;

$R^3$ and $R^4$ are each independently hydrogen, $C_{1-7}$-alkyl, $C_{1-7}$-alkoxy, halogen or di-$C_{1-7}$-alkylamino; or $R^2$ and $R^3$ or $R^3$ and $R^4$ which are attached to the same phenyl group or both $R^2$ attached to different phenyl groups, taken together, are —X—(CH$_2$)$_n$—Y—; or —X—(CF$_2$)—X— wherein X is O or C(O)O, Y is O or N($C_{1-7}$-alkyl); and n is an integer from 1 to 6.

Suitable diphosphine ligands can be selected from

| | | |
|---|---|---|
| (S)- or (R)-MeOBIPHEP | (S)- or (R)-(6,6'-Dimethoxybiphenyl-2,2'-diyl)bis(diphenylphosphine) |
| (S)- or (R)-6-MeO-2-Naphthyl-MeOBIPHEP | (S)- or (R)-(6,6'-Dimethoxybiphenyl-2,2'-diyl)bis(di-2-(6-methoxy)-naphthylphosphine) |
| (S)- or (R)-3,5-tBu-MeOBIPHEP | (S)- or (R)-(6,6'-Dimethoxy[1,1'-biphenyl]-2,2'-diyl)bis[bis(3,5-di-tert-butyl-phenyl)phosphine) |
| (S)- or (R)-3,5-iPr-MeOBIPHEP | (S)- or (R)-(6,6'-Dimethoxy[1,1'-biphenyl]-2,2'-diyl)bis[bis(3,5-di-iso-propyl-phenyl)phosphine) |
| (S)- or (R)-2-Furyl-MeOBIPHEP | (S)- or (R)-(6,6'-Dimethoxybiphenyl-2,2'-diyl)bis(di-2-furylphosphine) |
| (S)- or (R)-2-Thienyl-MeOBIPHEP | (S)- or (R)-(6,6'-Dimethoxy[1,1'-biphenyl]-2,2'-diyl)bis(bis(2-thienyl)phosphine) |
| (S)- or (R)-3-Thienyl-MeOBIPHEP | (S)- or (R)-(6,6'-Dimethoxy[1,1'-biphenyl]-2,2'-diyl)bis(bis(3-thienyl)phosphine) |
| (S)- or (R)-3,5-Xyl-MeOBIPHEP | (S)- or (R)-[6,6'-Dimethoxy[1,1'-biphenyl]-2,2'-diyl]bis[bis(3,5-dimethylphenyl)phosphine |
| (S)- or (R)-TMBTP | (S)- or (R)-2,2',5,5'-Tetramethyl-4,4'-bis(diphenylphosphino)-3,3'-bithiophene |

More preferred are the ligands of formula IVa, while the ligand (S)- or (R)-2-Furyl-MeOBIPHEP is the most preferred.

The most preferred Ru-catalysts of formula III are [Ru(OAc)$_2$((R)-2-Furyl-MeOBIPHEP)] or [Ru(OAc)$_2$((S)-2-Furyl-MeOBIPHEP)], wherein Ac stands for acetyl.

The diphosphine ligands as shown above are known in the art and are commercially available or can be prepared for example as described in the European Patent Application EP-A 0,398',132 (MeOBIPHEP, 3,5-iPr-MeOBIPHEP), the PCT Publication WO96/01831 or by T. Benincori et al., J. Org. Chem. 2000, 65, 2063 (TMBTP).

The metal complexes [Ru(OAc)$_2$(diphosphine)] are known in the art and are prepared for example as described in U.S. Pat. No. B 6,552,204 or synthesized in analogy to a general procedure reported in N. Feiken at al. Organometallics 1997, 16, 537.

The hydrogenation suitably takes place at a hydrogen pressure of 1 bar to 100 bar, preferably at 20 bar to 60 bar, more preferably at 35 to 45 bar.

The reaction temperature is selected between 20° C. and 100° C., preferably between 20° C. and 60° C., more preferably between 20° C. and 40° C.

As a rule the hydrogenation is carried out with a catalyst to substrate ratio (mol/mol) of 250 to 100,000, preferably of 1,000 to 20,000 more preferably of 5,000 to 15,000.

The reaction is usually carried out in a lower aliphatic alcohol as solvent. Most preferred solvent is methanol.

The enantiomeric purity of the resulting (3S,4S)-1-benzyl-4-halogen-aryl-pyrrolidine-3-carboxylic acid of formula I is as a rule so high that no further purification is necessary. Separation from the catalyst can happen by setting the reaction mixture to alkaline followed by extraction with an organic solvent and precipitating the product from the aqueous layer at the isoelectric point.

The following examples shall illustrate the invention without limiting it.

EXAMPLES

Abbreviations r.t.=room temperature, THF=tetrahydrofuran, TBME=tert. butyl methyl ether, LDA=lithium diisopropylamide Preparation of the Starting Compounds of Formula II

Example A

1-Benzyl-4-(4-chloro-phenyl)-2,5-dihydro-1H-pyrrole-3-carboxylic acid (IIa)

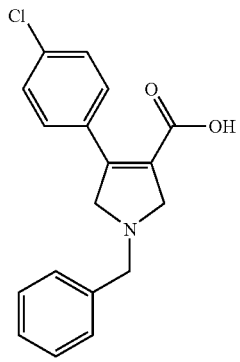

IIa a) (4-Chloro-phenyl)-propynoic acid ethyl ester (Va)

Under argon atmosphere, a four neck flask was charged with 1-chloro-4-iodo-benzene (130.0 g, 0.55 mol), bis(triphenylphosphine) palladium(II) chloride (7.57 g, 10.8 mmol, 2 mol %), copper(I) iodide (4.19 g, 22.0 mmol, 4 mol %) and dry THF (1.4 l). At r.t., cesium carbonate (355.3 g, 1.09 mol, 2 eq.) was added over 5 min. Afterwards propynoic acid ethyl ester (111.3 ml, 1.09 mol, 2 eq.) was added, and the reaction mixture was stirred overnight at 35° C. An additional portion of propynoic acid ethyl ester (11.1 ml, 0.11 mol, 0.2 eq.) was added, and the reaction was stirred for another 3 h at 35° C. The reaction mixture was evaporated to dryness, and the residue was taken up in toluene (0.5 l) and heptane (1 l). The resulting suspension was stirred at 40° C. for 1 h and filtered over celite. The filtrate was concentrated, and the product purified by silica gel filtration (toluene/heptane 1:2) to yield 72.6 g (61%) of Va as a light yellow solid.

b) 1-Benzyl-4-(4-chloro-phenyl)-2,5-dihydro-1H-pyrrole-3-carboxylic acid (IIa)

At r.t., a solution of N-(methoxymethyl)-N-(phenylmethyl)-N-(trimethylsilyl)methyl amine (116.8 g, 0.49 mol) in $CH_2Cl_2$ (260 ml) was added dropwise over 90 min to a stirred solution of (4-chloro-phenyl)-propynoic acid ethyl ester (72.0 g, 0.34 mol) and trifluoroacetic acid (2.5 ml, 0.03 mol) in $CH_2Cl_2$ (350 ml). The reaction mixture was stirred at 25° C. overnight and afterwards evaporated to dryness. The residue was dissolved in dioxane (0.8 l); an aqueous solution of NaOH (91.0 ml, 1.02 mol, 3 eq.) was added, and the resulting emulsion was stirred at r.t. for 48 h. The low boiling organic solvent was removed under vacuum, water (0.9 l) was added, and the aqueous layer was separated and washed with TBME (1 l). The aqueous layer was then acidified to a pH value of 2.5 by addition of 25% HCl. The resulting suspension was stirred overnight; the white precipitate was filtered off, washed with water and ethanol and dried under high vacuum to yield 62.0 g (60%) of IIa as a white solid.

ES-MS m/e: 312.4 (M–H$^+$).

Example B

1-Benzyl-4-(3,4-dichloro-phenyl)-2,5-dihydro-1H-pyrrole-3-carboxylic acid (IIb)

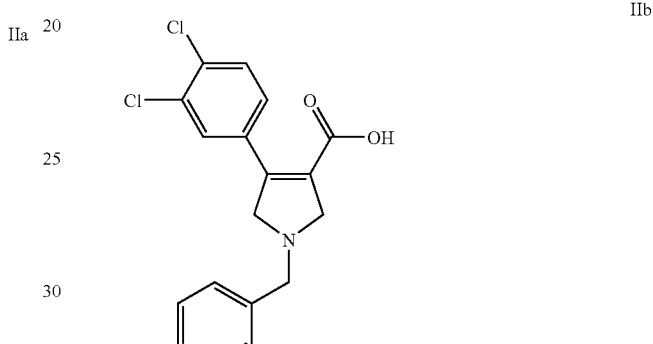

IIb a) (3,4-Dichloro-phenyl)-propynoic acid ethyl ester (Vb)

Under argon atmosphere, a four neck flask was charged with 1,2-dichloro-4-iodo-benzene (222.8 g, 0.80 mol), bis(triphenylphosphine) palladium(II) chloride (11.2 g, 16.0 mmol, 2 mol %), copper(I) iodide (6.09 g, 32.0 mmol, 4 mol %) and dry THF (2.4 l). At r.t., cesium carbonate (526.6 g, 1.60 mol, 2 eq.) was added over 5 minutes. Afterward, propynoic acid ethyl ester (168.6 ml, 1.60 mol, 2 eq.) was added, and the reaction mixture was stirred overnight at 35° C. An additional portion of propynoic acid ethyl ester (17.0 ml, 0.16 mol, 0.2 eq.) was added, and the reaction was stirred for another 4 h at 35° C. The reaction mixture was evaporated to dryness, and the residue was taken up in toluene (0.8 l) and heptane (1.6 l). The resulting suspension was stirred at 40° C. for 1 h and filtered over celite. The filtrate was concentrated, and the product was purified by silica gel filtration (toluene/heptane 1:2) to yield 175.0 g (89%) of Vb as a white solid.

b) 1-Benzyl-4-(3,4-dichloro-phenyl)-2,5-dihydro-1H-pyrrole-3-carboxylic acid (IIb)

At r.t., a solution of N-(methoxymethyl)-N-(phenylmethyl)-N-(trimethylsilyl)methyl amine (262.5 g, 1.06 mol) in $CH_2Cl_2$ (0.6 l) was added dropwise over 60 min to a solution of (3,4-dichloro-phenyl)-propynoic acid ethyl ester (172.0 g, 0.71 mol) and trifluoroacetic acid (5.4 ml, 0.07 mol) in $CH_2Cl_2$ (0.7 l). The reaction mixture was stirred at 25° C. for 2 h. The reaction mixture was then evaporated to dryness, and the residue was dissolved in dioxane (1.6 l). An aqueous solution of NaOH (1.0 l, 1.9 mol, 2.8 eq.) was added. The resulting emulsion was stirred at r.t. for 20 h, and the low boiling organic solvent was removed under vacuum. Water (2.0 l) was added, and the aqueous layer was separated and washed with TBME (2 times 1.2 l). The aqueous layer was then acidified to a pH value of 2.5 by addition of 25% HCl. The resulting suspension was then stirred overnight, and the white precipitate was filtered off, washed with water and ethanol and dried under high vacuum to yield 205.0 g (83%) of IIb as a white solid.

ES-MS m/e: 346.0 (M−H⁺).

Example C

1-Benzyl-4-(3,4-difluoro-phenyl)-2,5-dihydro-1H-pyrrole-3-carboxylic acid (IIc)

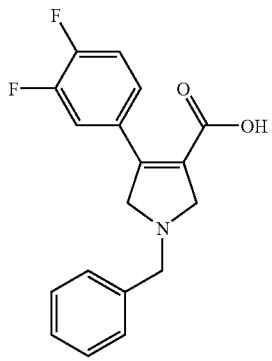

IIc a) (3,4-Difluoro-phenyl)-propynoic acid ethyl ester (Vc)

Under argon atmosphere, a four neck flask was charged with THF (135 ml) and 2 M LDA in THF (60.9 ml, 0.12 mol, 1.18 eq.) and cooled to −78° C. Propynoic acid ethyl ester (12.2 g, 0.12 mol, 1.18 eq.) dissolved in THF (36 ml) was added dropwise within 30 min. Then, ZnBr₂ (28.5 g, 0.12 mol, 1.2 eq.) dissolved in THF (45 ml) was added dropwise within 30 min. After the addition of 1,2-Difluoro-4-iodo-benzene (25.0 g, 0.10 mol) and tetrakis(triphenylphosphine) palladium(0) (6.02 g, 5.15 mmol, 5 mol %), the reaction mixture was allowed to warm to r.t. and stirred for another 3 h at the same temperature. The reaction mixture was diluted with diethylether and washed with saturated aqueous NH₄I, saturated aqueous NaHCO₃ and brine. The organic phase was dried with Na₂SO₄, concentrated under reduced pressure and dried under vacuum. The residue was purified by silica gel filtration (heptane/ethyl acetate 98:2) to yield 16.6 g (76%) of Vc as light yellow oil.

ES-MS m/c: 210 (M⁺).

b) 1-Benzyl-4-(3,4-difluoro-phenyl)-2,5-dihydro-1H-pyrrole-3-carboxylic acid (IIc)

At r.t., trifluoroacetic acid (0.11 ml, 1.34 mmol, 0.1 eq.) followed by N-(methoxymethyl)-N-(phenylmethyl)-N-(trimethylsilyl)methylamine (4.89 g, 20.2 mmol, 1.5 eq.) were added dropwise to a stirred solution of (3,4-difluoro-phenyl)-propynoic acid ethyl ester (2.83 g, 13.5 mmol) in CH₂Cl₂ (80 ml). The yellow solution was stirred at r.t. for 18 h. Trifluoroacetic acid (0.034 ml, 0.44 mmol, 0.033 eq.) and N-(methoxymethyl)-N-(phenylmethyl)-N-(trimethylsilyl) methylamine (1.66 g, 6.73 mmol, 0.5 eq.) were added, and the solution was stirred for 1 h. It was evaporated to dryness, and the residue was dissolved in dioxane (40 ml). An aqueous solution of NaOH (18.7 ml, 37.4 mmol, 2.8 eq.) was added. The resulting emulsion was stirred at r.t. for 18 h, and the low boiling organic solvent was removed under reduced pressure. Water (40 ml) was added, and the aqueous layer separated and washed twice with TBME (50 ml). The organic layers were washed with the same portion of water (15 ml). The combined aqueous layers were acidified by addition of aqueous 3M HCl (12.4 ml). The resulting suspension was stirred for 48 h at r.t. The white precipitate was filtered off, washed with water and ethanol and dried under high vacuum to yield 4.25 g (58%) of IIc as a white solid.

ES-MS m/e: 316.3 (M+H⁺).

Example D

1-Benzyl-4-(4-chloro-3-fluoro-phenyl)-2,5-dihydro-1H-pyrrole-3-carboxylic acid (IId)

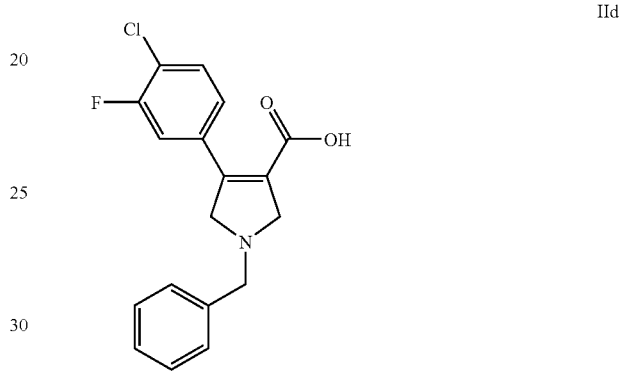

IId a) (4-Chloro-3-fluoro-phenyl)-propynoic acid ethyl ester (Vd)

Under argon atmosphere, a four neck flask was charged with 1-chloro-2-fluoro-4-iodo-benzene (50.5 g, 0.20 mol), bis(triphenylphosphine) palladium(II) chloride (2.76 g, 3.94 mmol, 2 mol %), copper(I) iodide (1.50 g, 7.80 mol, 4 mol %) and dry THF (600 ml). At r.t., cesium carbonate (128.3 g, 0.39 mol, 2 eq.) was added over 5 min. Finally, propynoic acid ethyl ester (38.6 g, 0.39 mol, 2 eq.) was added, and the reaction was stirred for 48 h at 35° C. The reaction mixture was evaporated to dryness, and the residue was taken up in toluene (50 ml) and heptane (100 ml). The resulting suspension was stirred at 40° C. for 1 h and filtered afterward over celite. The filtrate was concentrated, and the product was purified by silica gel filtration (toluene/heptane 1:2) to yield 38.8 g (87%) of the Vd as a light yellow solid.

ES-MS m/e: 227.2 (M−H⁺).

b) 1-Benzyl-4-(4-chloro-3-fluoro-phenyl)-2,5-dihydro-1H-pyrrole-3-carboxylic acid (IId)

At r.t., a solution of N-(methoxymethyl)-N-(phenylmethyl)-N-(trimethylsilyl)methyl amine (61.3 g, 0.26 mol) in CH₂Cl₂ (120 ml) was added dropwise over 90 minutes to a stirred solution of (4-chloro-3-fluoro-phenyl)-propynoic acid ethyl ester (39.0 g, 0.17 mol) and trifluoroacetic acid (1.30 ml, 0.02 mol) in CH₂Cl₂ (170 ml). The reaction mixture was stirred at 25° C. for 72 h and afterward evaporated to dryness. The residue was dissolved in dioxane (390 ml). An aqueous solution of NaOH (45.0 ml, 0.48 mol, 2.8 eq.) was added, and the resulting emulsion was stirred at r.t. for 18 h. The low boiling organic solvent was removed under vacuum. Water (100 ml) was added, the aqueous layer was separated and washed with TBME (2 times 100 ml). The aqueous layer was then acidified to a pH value of 2.5 by addition of 25% HCl. The resulting suspension was stirred overnight and the white precipitate was filtered off, washed with water and ethanol and dried under high vacuum to yield 42.0 g (75%) of IId as a white solid.

ES-MS m/e: 330.1 (M–H$^+$).

Synthesis of catalyst [Ru(OAc)$_2$((R)-2-Furyl-MeO-BIPHEP)] and of catalyst [Ru(OAc)$_2$((S)-2-Furyl-MeOBIPHEP)]

Example E

[Ru(OAc)$_2$((R)-2-Furyl-MeOBIPHEP)]

A 500-ml round bottomed flask was charged under argon with (R)-2-Furyl-MeOBIPHEP (30.0 g, 51.5 mmol), [Ru(OAc)$_2$(p-cymene)] (18.75 g, 53.04 mmol) and toluene (525 ml). The resulting brown suspension was stirred at 80° C. for 24 h. The resulting yellow-brown suspension was concentrated on vacuum to a total volume of 250 ml and stirred for 1 h at 0-5° C. The suspension was filtered, and the filter cake was washed with toluene (100 ml) and pentane (150 ml) and dried at r.t. for 16 h under vacuum to yield 36.5 g (93%) of [Ru(OAc)$_2$((R)-2-Furyl-MeOBIPHEP)] as a yellow solid.

$^{31}$P-NMR (CDCl$_3$): 31.8 ppm (singlett). FT-MS m/e: 762 (M$^+$).

[Ru(OAc)$_2$((S)-2-Furyl-MeOBIPHEP)]

A 50-ml round bottomed flask was charged under argon with (S)-2-Furyl-MeOBIPHEP (500 mg, 0.92 mmol), [Ru(OAc)$_2$(p-cymene)] (330 mg, 0.93 mmol) and toluene (10 ml). The resulting brown suspension was stirred at 80° C. for 5 h. The reaction mixture was concentrated on vacuum to a total volume of 2 ml; pentane (20 ml) was added, and the mixture was stirred for 30 min at 0-5° C. The suspension was filtered, and the filter cake was washed with pentane (20 ml) and dried at r.t. for 16 h under vacuum to yield 569 mg (81%) of [Ru(OAc)$_2$((S-2-Furyl-MeOBIPHEP)] as a yellow solid.

$^{31}$P-NMR (CDCl$_3$): 31.7 ppm (singlett). FT-MS m/e: 762 (M$^+$).

HYDROGENATION EXAMPLES

Example 1

(3S,4S)-1-Benzyl-4-(4-chloro-phenyl)-pyrrolidine-3-carboxylic acid, (S,S)-Ia

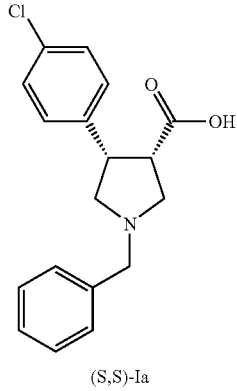 [SMILES: O=C(O)[C@@H]1CN(Cc2ccccc2)C[C@@H]1c1ccc(Cl)cc1]

(S,S)-Ia

A 185-ml stainless steel autoclave was charged under argon in a glove box (O$_2$ content≦2 ppm) with 1-benzyl-4-(4-chloro-phenyl)-2,5-dihydro-1H-pyrrole-3-carboxylic acid monohydrate (5.00 g, 15.1 mmol), [Ru(OAc)$_2$((R)-2-Furyl-MeOBIPHEP)] (3.83 mg, 5.02×10$^{-6}$ mol, S/C 3,000) and methanol (150 ml). The asymmetric hydrogenation was run for 20 h at 30° C. under 40 bar of hydrogen (99.6% conversion, 99.3% (S,S)-Ia with >99.9% ee). After the pressure was released, the white suspension was stirred at 0-5° C. (ice-bath) for 2 h and filtered. The filter cake was washed with 20 ml ice-cold methanol and dried under vacuum at 40° C. to yield 4.75 g (99%) of (S,S)-Ia with 99.0% purity and >99.9% ee.

ES-MS m/e: 316.1 (M+H$^+$).

HPLC method for purity and ee determination: Chirobiotic V column (No. 461, 25 cm*4.6 mm), 55% ammonium acetate pH 6 buffer/45% acetonitrile, flow 1 ml/min, 25° C., 220 nm, sample preparation: 1 mg in 1 ml acetonitrile. Retention times: IIa (3.7 min), (R,S)-/(S,R)-Ia (4.3 min), (S,S)-Ia (4.9 min), (R,R)-Ia (5.4 min).

Example 2

(3S,4S)-1-Benzyl-4-(4-chloro-phenyl)-pyrrolidine-3-carboxylic acid, (S,S)-Ia

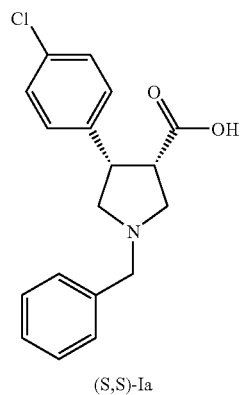 [SMILES: O=C(O)[C@@H]1CN(Cc2ccccc2)C[C@@H]1c1ccc(Cl)cc1]

(S,S)-Ia

A 12-l stainless steel autoclave was charged on air with 1-benzyl-4-(4-chloro-phenyl)-2,5-dihydro-1H-pyrrole-3-carboxylic acid monohydrate (180.0 g, 0.54 mol), [Ru(OAc)$_2$((R)-2-Furyl-MeOBIPHEP)] (413.2 mg, 0.54 mmol, S/C 1,000) and methanol (7.1 l). The asymmetric hydrogenation was run for 20 h at 30° C. under 40 bar of hydrogen (99.3% conversion). After the pressure was released, a sample of the white suspension was evaporated to dryness affording crude (S,S)-Ia with 99.0% purity and >99.9% ee. The reaction suspension was concentrated to a volume of 1.8 l and stirred for 1 h at 0-5° C. After filtration, the filter cake was washed with cold methanol and dried on vacuum to yield 176.0 g (>99%) of (S,S)-Ia as a white solid with 99.0% purity and >99.9% ee.

Examples 3a-c (3S,4S)-1-Benzyl-4-(4-chloro-phenyl)-pyrrolidine-3-carboxylic acid, (S,S)-Ia

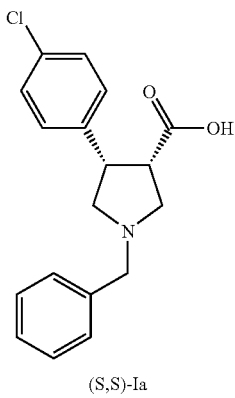 [SMILES: O=C(O)[C@@H]1CN(Cc2ccccc2)C[C@@H]1c1ccc(Cl)cc1]

(S,S)-Ia

A 185-ml stainless steel autoclave was charged under argon in a glove box (O$_2$ content≦2 ppm) with 1-benzyl-4-(4-chloro-phenyl)-2,5-dihydro-1H-pyrrole-3-carboxylic acid monohydrate (1.00 g, 3.01 mmol), [Ru(OAc)$_2$((R)-2-Furyl-MeOBIPHEP] (0.21 mg, 0.30×10$^{-6}$ mol, S/C 10,000) and methanol (30 ml). The asymmetric hydrogenation was run for 20 h at 30° C. under 40 bar of hydrogen (87.0% conversion). After the pressure was released, the white suspension was evaporated to dryness to yield 0.96 g (86%) of crude (S,S)-Ia with 88.5% purity and 98.5% ee.

The reactions in Table 1 were performed according to the procedure described above using triethylamine as additive.

TABLE 1

| Example | Additive (Amount) | Conversion (%) | (S,S)-Ib Purity (%) | (S,S)-Ib % ee |
|---|---|---|---|---|
| 3b | NEt$_3$ (1 eq. rel. to substrate) | 73.8 | 72.8 | 98.6 |
| 3c | NEt$_3$ (0.5 eq. rel. to substrate) | 90.9 | 90.8 | 98.9 |

Examples 4a-c (3S,4S)-1-Benzyl-4-(4-chloro-phenyl)-pyrrolidine-3-carboxylic acid, (S,S)-Ia

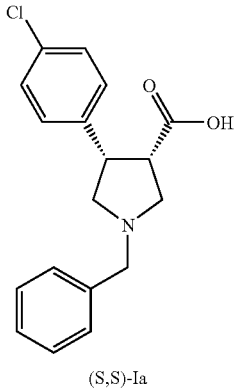 [SMILES: O=C(O)[C@@H]1CN(Cc2ccccc2)C[C@@H]1c1ccc(Cl)cc1]

(S,S)-Ia

A 185-ml stainless steel autoclave was charged under argon in a glove box (O$_2$ content≦2 ppm) with 1-benzyl-4-(4-chloro-phenyl)-2,5-dihydro-1H-pyrrole-3-carboxylic acid monohydrate (1.00 g, 3.01 mmol), [Ru(OAc)$_2$((R)-2-Furyl-MeOBIPHEP)] (0.77 mg, 1.00×10$^{-6}$ mol, S/C 3000) and 30 ml methanol. The asymmetric hydrogenation was run for 20 h at 30° C. under 40 bar of hydrogen (99.8% conversion). After the pressure was released, the white suspension was evaporated to dryness to yield 0.96 g (99%) of crude (S,S)-Ia with 99.1% purity and >99.9% ee.

The reactions in Table 2 were performed according to the procedure described above using alternative solvents to methanol.

TABLE 2

| Example | Solvent | Conversion (%) | (S,S)-Ia Purity (%) | (S,S)-Ia % ee |
|---|---|---|---|---|
| 4b | ethanol | 20.3 | 19.8 | 98.7 |
| 4c | 2-propanol | 17.3 | 15.2 | 92.1 |

Example 5

(3S,4S)-1-Benzyl-4-(3,4-dichloro-phenyl)-pyrrolidine-3-carboxylic acid, (S,S)-Ib

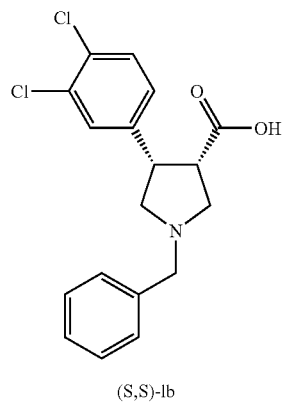 [SMILES: O=C(O)[C@@H]1CN(Cc2ccccc2)C[C@@H]1c1ccc(Cl)c(Cl)c1]

(S,S)-Ib

A 35-ml autoclave was charged under argon in a glove box (O$_2$ content≦2 ppm) with the hydrochloride salt of 1-benzyl-4-(3,4-dichloro-phenyl)-2,5-dihydro-1H-pyrrole-3-carboxylic acid (0.50 g, 1.30 mmol), [Ru(OAc)$_2$((R)-2-Furyl-MeOBIPHEP)] (3.96 mg, 5.30×10$^{-6}$ mol, S/C 250), triethylamine (0.19 ml, 1.32 mmol) and methanol (15 ml). The asymmetric hydrogenation was run for 20 h at 30° C. under 40 bar of hydrogen (99.9% conversion). After the pressure was released, the formed white suspension was evaporated to dryness to yield 0.51 g (99%) of crude (S,S)-Ib with 99.6% purity and 99.4% ee.

The crude product was dissolved in 0.1 M NaOH (23 ml). TBME (20 ml) was added, the aqueous layer was separated and diluted with water (23 ml). Under stirring 0.2 M HCl was added until pH 6.5. The formed precipitate was filtered off and washed with water. The filter cake was dissolved in methanol, and the colourless solution was evaporated to dryness to yield 0.31 g (68%) of (S,S)-Ia with 99.7% purity and 99.8% ee.

ES-MS m/e: 350.3 (M$^+$).

HPLC method for purity and ee determination: Chirobiotic V column (No. 461, 25 cm*4.6 mm), 55% ammonium acetate pH 6 buffer/45% acetonitrile, flow 1 ml/min, 25° C., 220 nm, sample preparation: 1 mg in 1 ml acetonitrile. Retention times: IIb (3.7 min), (R,S)-/(S,R)-Ib (4.4 min), (S,S)-Ib (5.1 min), (R,R)-Ib (6.4 min), (S)-Vb (14.9 min).

Example 6

(3S,4S)-1-Benzyl-4-(3,4-dichloro-phenyl)-pyrrolidine-3-carboxylic acid, (S,S)-Ib

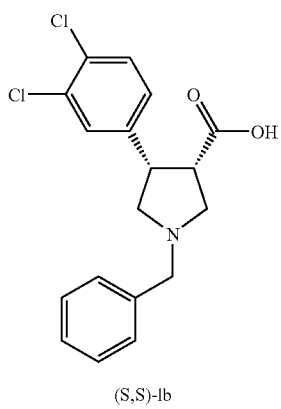 [SMILES: O=C(O)[C@@H]1CN(Cc2ccccc2)C[C@@H]1c1ccc(Cl)c(Cl)c1]

(S,S)-Ib

A 2-l Hastelloy C4 autoclave was charged under argon with 1-benzyl-4-(3,4-dichloro-phenyl)-2,5-dihydro-1H-pyrrole-3-carboxylic acid (30.0 g, 86.15 mmol), [Ru(OAc)$_2$((R)-2-Furyl-MeOBIPHEP)] (262.5 mg, 0.34 mmol, S/C 250) and methanol (0.9 l). The asymmetric hydrogenation was run for 18 h at 30° C. and an additional 2 h at 60° C. under 40 bar of hydrogen (99.8% conversion). After the pressure was released, the formed white suspension was evaporated to dryness to yield 32.6 g (>99%) of crude (S,S)-Ib with 97.0% purity and >99.9% ee.

The crude product was dissolved in 1M NaOH (140 ml). TBME (200 ml) was added, the aqueous layer was separated and diluted with water (360 ml). Under stirring 2 M HCl (81 ml) were added (pH 6.5). The formed precipitate was filtered off and washed with water. The filter cake was dissolved in methanol, and the colourless solution was evaporated to dryness to yield 27.2 g (90%) of (S,S)-Ib with 99.5% purity and >99.9% ee.

Examples 7a-g

(3S,4S)-1-Benzyl-4-(3,4-dichloro-phenyl)-pyrrolidine-3-carboxylic acid, (S,S)-Ib

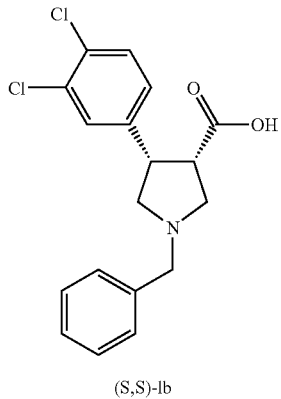

(S,S)-Ib

A 185-ml stainless steel autoclave was charged under argon in a glove box (O$_2$ content≦2 ppm) with 1-benzyl-4-(3,4-dichloro-phenyl)-2,5-dihydro-1H-pyrrole-3-carboxylic acid (1.00 g, 2.87 mmol), [Ru(OAc)$_2$((R)-TMBTP)] (1.16 mg, 1.44×10$^{-6}$ mol, S/C 2',000) and methanol (30 ml). The asymmetric hydrogenation was run for 20 h at 30° C. under 40 bar of hydrogen (18.5% conversion). After the pressure was released, the off-white suspension was evaporated to dryness to yield 0.98 g (12%) of crude (S,S)-Ib with 12.1% purity and 94.5% ee.

The reactions in Table 3 were performed according to the procedure described above employing alternative catalysts.

TABLE 3

| Example | Catalyst | Conversion (%) | (S,S)-Ib Purity (%) | (S,S)-Ib % ee |
|---|---|---|---|---|
| 7b | [Ru(OAc)$_2$((S)-(6-MeO-2-Naphtyl)-MeOBIPHEP] | 76.2 | 67.9[1] | 97.4[1] |
| 7c | [Ru(OAc)$_2$((R)-3,5-iPr-MeOBIPHEP)] | 26.9 | 19.0 | 90.0 |
| 7d | [Ru(OAc)$_2$((R)-MeOBIPHEP)] | 38.3 | 30.4 | 97.4 |
| 7e | [Ru(OAc)$_2$((R)-3,5-tBu-MeOBIPHEP)] | 4.1 | 1.6 | 67.6 |
| 7f | [Ru(OAc)$_2$((S)-(3-Thienyl)-MeOBIPHEP)] | 62.5 | 60.0[1] | 98.0[1] |
| 7g | [Ru(OAc)$_2$((S)-(2-Thienyl)-MeOBIPHEP)] | 25.1 | 25.0[1] | 99.9[1] |

[1](R,R)-Ib was formed in excess

Examples 7h

(3R,4R)-1-Benzyl-4-(3,4-dichloro-phenyl)-pyrrolidine-3-carboxylic acid, (R,R)-Ib

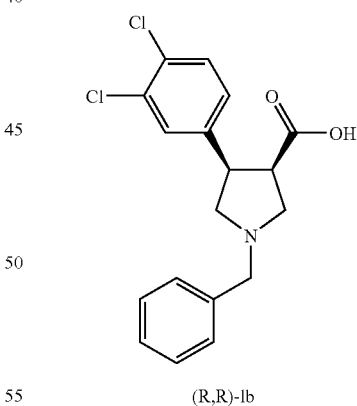

(R,R)-Ib

A 2-l Hastelloy C4 autoclave was charged under argon with the hydrochloride salt of 1-benzyl-4-(3,4-dichloro-phenyl)-2,5-dihydro-1H-pyrrole-3-carboxylic acid (67.0 g, 174.17 mmol), [Ru(OAc)$_2$((S)-2-Furyl-MeOBIPHEP)] (2.65 g, 3.48 mmol, S/C 50), triethylamine (17.62 g, 174.17 mmol) and methanol (1.3 l). The asymmetric hydrogenation was run for 20 h at 30° C. under 40 bar of hydrogen (98.9% conversion). After the pressure was released, the formed gray suspension was evaporated to dryness to yield 88.8 g of crude (R,R)-Ib with 95.7% purity and 99.3% ee.

The crude product was dissolved in 1M NaOH (350 ml). TBME (600 ml) was added; the aqueous layer was separated and diluted with water (900 ml). Under stirring 2 M HCl (180 ml) were added (pH 6.0). The formed precipitate was filtered off and washed with water. The filter cake was suspended in methanol/water (1:2) and the mixture was heated to reflux. After cooling to room temperature, the suspension was filtered. The filter cake was washed with methanol and dried to yield 46.15 g (74%) of (R,R)-Ib with 97.3% purity and 99.8% ee.

Example 8

(3S,4S)-1-Benzyl-4-(3,4-dichloro-phenyl)-pyrrolidine-3-carboxylic acid, (S,S)-Ib

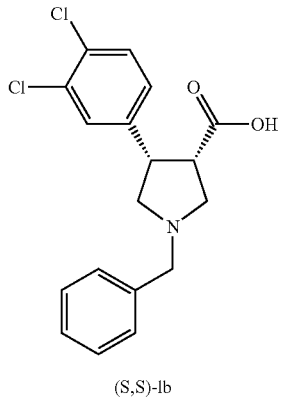

(S,S)-Ib

A 185-ml stainless steel autoclave was charged under argon in a glove box ($O_2$ content≦2 ppm) with 1-benzyl-4-(3,4-dichloro-phenyl)-2,5-dihydro-1H-pyrrole-3-carboxylic acid (1.00 g, 2.87 mmol), [Ru(OAc)$_2$((R)-2-Furyl-MeOBI-PHEP)] (0.44 mg, $0.57 \times 10^{-6}$ mol, S/C 5'000) and methanol (30 ml). The asymmetric hydrogenation was run for 20 h at 80° C. under 40 bar of hydrogen (99.7% conversion). After the pressure was released, the formed white suspension was evaporated to dryness to yield 1.02 g (99%) of crude (S,S)-Ib with 97.6% purity and 99.2% ee.

Example 9

(3S,4S)-1-Benzyl-4-(3,4-dichloro-phenyl)-pyrrolidine-3-carboxylic acid, (S,S)-Ib

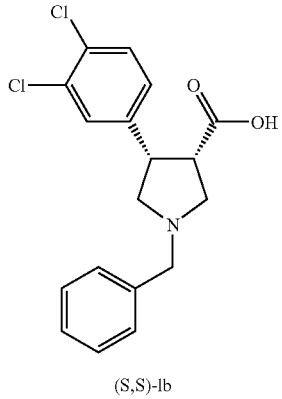

(S,S)-Ib

A 185-ml stainless steel autoclave was charged under argon in a glove box ($O_2$ content≦2 ppm) with 1-benzyl-4-(3,4-dichloro-phenyl)-2,5-dihydro-1H-pyrrole-3-carboxylic acid (1.00 g, 2.87 mmol), [Ru(OAc)$_2$((R)-2-Furyl-MeOBI-PHEP)] (0.22 mg, $0.29 \times 10^{-6}$ mol, S/C 10'000) and methanol (30 ml). The asymmetric hydrogenation was run for 20 h at 80° C. under 40 bar of hydrogen (99.8% conversion). After the pressure was released, the formed white suspension was evaporated to dryness to yield 1.03 g (>99%) of crude (S,S)-Ib with 98.0% purity and 97.6% ee.

Example 10

(3S,4S)-1-Benzyl-4-(3,4-difluoro-phenyl)-pyrrolidine-3-carboxylic acid, (S,S)-Ic

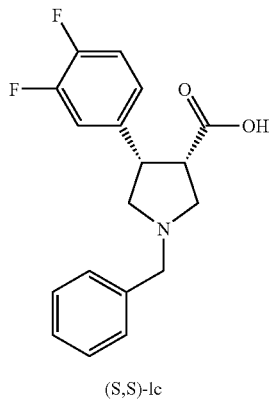 [SMILES: O=C(O)[C@@H]1CN(Cc2ccccc2)C[C@@H]1c1ccc(F)c(F)c1]

(S,S)-Ic

A 35-ml stainless steel autoclave was charged under argon in a glove box ($O_2$ content≦2 ppm) with 1-benzyl-4-(3,4-difluoro-phenyl)-2,5-dihydro-1H-pyrrole-3-carboxylic acid (50.0 mg, 0.16 mmol), [Ru(OAc)$_2$((R)-2-Furyl-MeOBI-PHEP)] (1.21 mg, $1.59 \times 10^{-6}$ mol, S/C 100) and methanol (1.5 ml). The asymmetric hydrogenation was run for 20 h at 30° C. under 40 bar of hydrogen (98.6% conversion). After the pressure was released, the white suspension was evaporated to dryness to yield 51.9 mg (98%) of crude (S,S)-Ic with 95.6% purity and >99.9% ee.

MS m/e: 318.1 (M+H$^+$).

HPLC method for purity and ee determination: Chirobiotic V column (No. 461, 25 cm*4.6 mm), 55% ammonium acetate pH 6 buffer/45% acetonitrile, flow 1 mL/min, 25° C., 220 nm, sample preparation: 1 mg in 1 ml acetonitrile. Retention times: IIc (3.6 min), (R,S)-/(S,R)-Ic (4.1 min), (S,S)-Ic (4.5 min), (R,R)-Ic (4.9 min).

Example 11

(3S,4S)-1-Benzyl-4-(3,4-difluoro-phenyl)-pyrrolidine-3-carboxylic acid, (S,S)-Ic

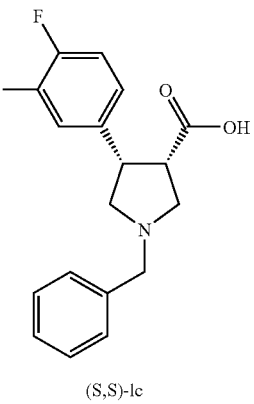

(S,S)-Ic

A 185-ml stainless steel autoclave was charged under argon in a glove box (O₂ content≦2 ppm) with 1-benzyl-4-(3,4-difluoro-phenyl)-2,5-dihydro-1H-pyrrole-3-carboxylic acid (2.00 g, 6.34 mmol), [Ru(OAc)₂((R)-2-Furyl-MeOBIPHEP)] (9.66 mg, 12.7×10⁻⁶ mol, S/C 500), triethylamine (342.0 mg, 6.34 mmol) and methanol (60 ml). The asymmetric hydrogenation was run for 20 h at 30° C. under 40 bar of hydrogen (>99% conversion). After the pressure was released, the formed white suspension was evaporated to dryness to yield 2.00 g of crude (S,S)-Ic as its ammonium salt with >99.9% purity and >99.9% ee. The salt was dissolved in 1M NaOH (10 ml). TBME (16 ml) was added to the reaction mixture, the aqueous layer was separated and diluted with water (40 ml). Under stirring 2 M HCl (7.1 ml) were added (pH 6.5). The formed precipitate was filtered off and washed with water. The filter cake was dissolved in methanol and the colourless solution evaporated to dryness to yield 1.70 g (88%) of (S,S)-Ic with 98.3% purity and >99.9% ee.

Example 12

(3S,4S)-1-Benzyl-4-(4-chloro-3-fluoro-phenyl)-pyrrolidine-3-carboxylic acid, (S,S)-Id

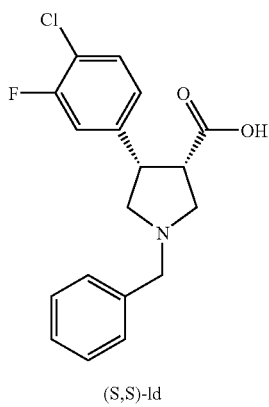 [SMILES: O=C(O)[C@@H]1CN(Cc2ccccc2)C[C@@H]1c1ccc(Cl)c(F)c1]

(S,S)-Id

A 185-ml stainless steel autoclave was charged under argon in a glove box (O₂ content≦2 ppm) with 1-benzyl-4-(4-chloro-3-fluoro-phenyl)-2,5-dihydro-1H-pyrrole-3-carboxylic acid (1.00 g, 3.01 mmol), [Ru(OAc)₂((R)-2-Furyl-MeOBIPHEP)] (4.59 mg, 6.03×10⁻⁶ mol, S/C 500) and methanol (30 ml). The asymmetric hydrogenation was run for 20 h at 30° C. under 40 bar of hydrogen (99.5% conversion). After the pressure was released, the white suspension was evaporated to dryness to yield 1.03 g (>99%) of crude (S,S)-Id with 98.3% purity and 99.1% ee.

ES-MS m/e: 332.1 (M−H⁺).

HPLC method for purity and ee determination: Chirobiotic V column (No. 461, 25 cm*4.6 mm), 55% ammonium acetate pH 6 buffer/45% acetonitrile, flow 1 ml/min, 25° C., 220 nm, sample preparation: 1 mg in 1 ml acetonitrile. Retention times: IId (3.5 min), (R,S)-/(S,R)-Id (4.3 min), (S,S)-Ic (4.7 min), (R,R)-Id (5.4 min).

Example 13

(3S,4S)-1-Benzyl-4-(4-chloro-3-fluoro-phenyl)-pyrrolidine-3-carboxylic acid, (S,S)-Id

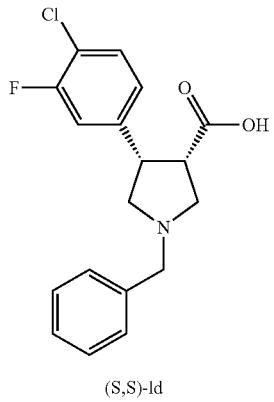 [SMILES: O=C(O)[C@@H]1CN(Cc2ccccc2)C[C@@H]1c1ccc(Cl)c(F)c1]

(S,S)-Id

A 185-ml stainless steel autoclave was charged under argon in a glove box (O₂ content≦2 ppm) with 1-benzyl-4-(4-chloro-3-fluoro-phenyl)-2,5-dihydro-1H-pyrrole-3-carboxylic acid (1.00 g, 3.01 mmol), [Ru(OAc)₂((R)-2-Furyl-MeOBIPHEP)] (4.59 mg, 6.03×10⁻⁶ mol, S/C 500), triethylamine (305.0 mg, 3.01 mmol) and methanol (30 ml). The asymmetric hydrogenation was run for 20 h at 30° C. under 40 bar of hydrogen (99.2% conversion). After the pressure was released, the formed white suspension was evaporated to dryness to yield 1.08 g of crude (S,S)-Id as its ammonium salt with 97.3% purity and >99.9% ee.

The salt was dissolved in 1M NaOH (10 ml). TBME (16 ml) was added to the reaction mixture; the aqueous layer was separated and diluted with water (40 ml). Under stirring 2 M HCl (8.2 ml) was added (pH 6.5), and the formed precipitate was filtered off and washed with water. The filter cake was dissolved in methanol, and the colourless solution was evaporated to dryness to yield 1.00 g (97%) of (S,S)-Id with 97.5% purity and >99.9% ee.

Example 14

(3S,4S)-1-Benzyl-4-(4-chloro-3-fluoro-phenyl)-pyrrolidine-3-carboxylic acid, (S,S)-Id

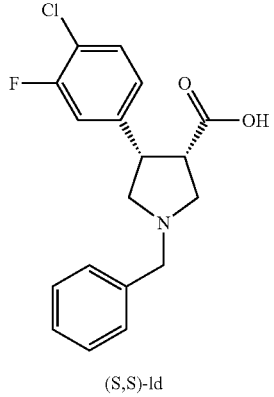 [SMILES: O=C(O)[C@@H]1CN(Cc2ccccc2)C[C@@H]1c1ccc(Cl)c(F)c1]

(S,S)-Id

A 2-l Hastelloy C4 autoclave was charged under argon with 1-benzyl-4-(4-chloro-3-fluoro-phenyl)-2,5-dihydro-1H-pyrrole-3-carboxylic acid (30.0 g, 90.4 mmol), [Ru(OAc)₂((R)-2-Furyl-MeOBIPHEP)] (275.5 mg, 0.36 mmol, S/C 250) and methanol (1.2 l). The asymmetric hydrogenation was run for 20 h at 30° C. under 40 bar of hydrogen (99.2% conversion). After the pressure was released, a sample of the white suspension was evaporated to dryness. Crude (S,S)-Id was obtained with 97.9% purity and >99.9% ee.

Examples 15

(3R,4R)-1-Benzyl-4-(4-chloro-3-fluoro-phenyl)-pyrrolidine-3-carboxylic acid, (R,R)-Id

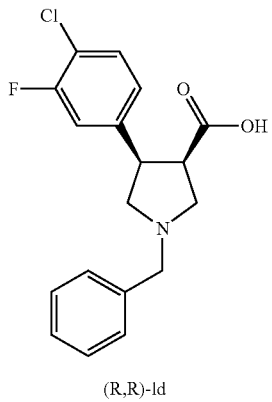 [SMILES: O=C(O)[C@H]1CN(Cc2ccccc2)C[C@H]1c1ccc(Cl)c(F)c1]

(R,R)-Id

A 2-l Hastelloy C4 autoclave was charged under argon with the hydrochloride salt of 1-benzyl-4-(4-chloro-3-fluoro-phenyl)-2,5-dihydro-1H-pyrrole-3-carboxylic acid (61.3 g, 166.47 mmol), [Ru(OAc)$_2$((S)-2-Furyl-MeOBIPHEP)] (2.54 g, 3.33 mmol, S/C 50), triethylamine (16.84 g, 166.46 mmol) and methanol (1.3 l). The asymmetric hydrogenation was run for 20 h at 30° C. under 40 bar of hydrogen (99.6% conversion). After the pressure was released, the formed gray suspension was evaporated to dryness to yield 98.0 g of crude (R,R)-Id with 97.6% purity and 99.6% ee.

The crude product was dissolved in 1M NaOH (330 ml). TBME (600 ml) was added; the aqueous layer was separated and diluted with water (800 ml). Under stirring 2 M HCl (165 ml) were added (pH 6.3). The formed precipitate was filtered off and washed with water. The filter cake was suspended in methanol/water (1:2), and the mixture was heated to reflux. After cooling to room temperature, the suspension was filtered. The filter cake was washed with methanol and dried to yield 49.0 g (83%) of (R,R)-Id with 99.6% purity and 99.6% ee.

Examples 16

(3R,4R)-1-Benzyl-4-(3,4-difluoro-phenyl)-pyrrolidine-3-carboxylic acid, (R,R)-Ic

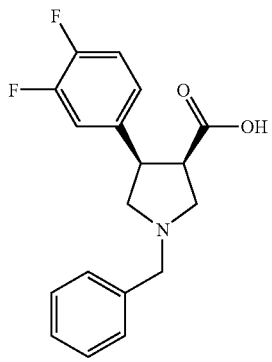

(R,R)-Ic

A 2-l Hastelloy C4 autoclave was charged under argon with the hydrochloride salt of 1-benzyl-4-(3,4-difluoro-phenyl)-2,5-dihydro-1H-pyrrole-3-carboxylic acid (45.0 g, 127.92 mmol), [Ru(OAc)$_2$((S)-2-Furyl-MeOBIPHEP)] (1.95 g, 2.56 mmol, S/C 50), triethylamine (12.94 g, 127.92 mmol) and methanol (1.3 l). The asymmetric hydrogenation was run for 20 h at 30° C. under 40 bar of hydrogen (>99.9% conversion). After the pressure was released, the formed gray suspension was evaporated to dryness to yield 58.9 g of crude (R,R)-Ic with 99.0% purity and >99.9% ee.

The crude product was dissolved in 1M NaOH (200 ml). TBME (400 ml) was added; the aqueous layer was separated and diluted with water (800 ml). Under stirring 2 M HCl (105 ml) were added (pH 5.5). The formed precipitate was filtered off and washed with water. The filter cake was suspended in methanol/water (1:2), and the mixture was heated to reflux. After cooling to room temperature, the suspension was filtered. The filter cake was washed with methanol and dried to yield 29.10 g (71%) of (R,R)-Ic with 99.5% purity and >99.9% ee.

The invention claimed is:
1. A process for the preparation of (3S,4S)- or (3R,4R)-1-benzyl-4-aryl-pyrrolidine-3-carboxylic acids of formula I

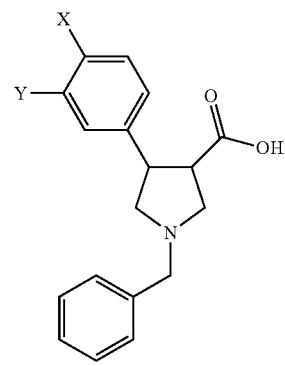

I or salts thereof,
wherein
X and Y are each independently hydrogen or a halogen atom, with the proviso that at least one of X or Y is a halogen atom,
comprising catalytic homogeneous enantioselective hydrogenation of a compound of formula II

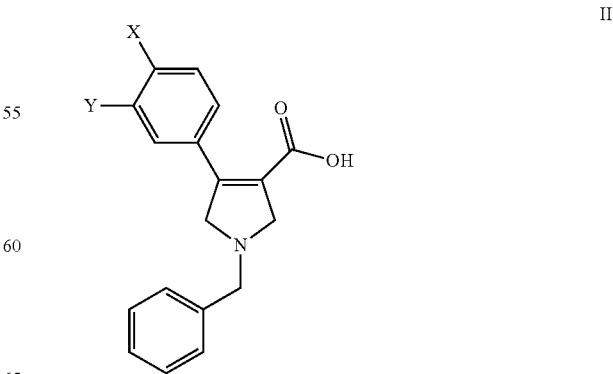

II or salts thereof, wherein X and Y are as above, in the presence of a Ru-catalyst selected from the group consisting of [Ru(OAc)$_2$((R)-2-furyl-MeOBIPHEP)] and [Ru(OAc)$_2$((S)-2-furyl-MeOBIPHEP)].

2. The process of claim 1, wherein X or Y are chlorine or fluorine.

3. The process of claim 1 wherein the hydrogenation is carried out at a pressure of 1 bar to 100 bar.

4. The process of claim 3 wherein the hydrogenation is carried out at a pressure of 20 bar to 60 bar.

5. The process of claim 1, wherein the hydrogenation is carried out at a temperature of 20° C. to 100° C.

6. The process of claim 5, wherein the hydrogenation is carried out at a temperature of 20° C. to 60° C.

7. The process of claim 1, wherein the hydrogenation is carried out with a catalyst to substrate ratio (mol/mol) of 250 to 100,000.

8. The process of claim 7, wherein the hydrogenation is carried out with a catalyst to substrate ratio (mol/mol) of 1,000 to 20,000.

9. The process of claim 1, wherein the hydrogenation is carried out in a lower aliphatic alcohol as solvent.

10. The process of claim 9, wherein the lower aliphatic alcohol is methanol.

11. The process of claim 1, wherein the compound of formula II is selected from 1-benzyl-4-(4-chloro-phenyl)-2,5-dihydro-1H-pyrrole-3-carboxylic acid monohydrate;

1-benzyl-4-(3,4-dichloro-phenyl)-2,5-dihydro-1H-pyrrole-3-carboxylic acid;

1-benzyl-4-(3,4-difluoro-phenyl)-2,5-dihydro-1H-pyrrole-3-carboxylic acid; and 1-benzyl-4-(4-chloro-3-fluoro-phenyl)-2,5-dihydro-1H-pyrrole-3-carboxylic acid.

\* \* \* \* \*